United States Patent [19]

Parker et al.

[11] Patent Number: 5,720,099

[45] Date of Patent: Feb. 24, 1998

[54] THIN FILM FABRICATION TECHNIQUE FOR IMPLANTABLE ELECTRODES

[75] Inventors: John L. Parker, Lane Cove; Claudiu Treaba, Wollstonecraft, both of Australia

[73] Assignee: Cochlear Limited, Lane Cove, Australia

[21] Appl. No.: 641,537

[22] Filed: May 1, 1996

[51] Int. Cl.$^6$ ................................................ H05K 1/14
[52] U.S. Cl. ............................ 29/825; 29/25.35; 29/830; 437/183
[58] Field of Search ......................... 29/25.35, 825, 29/830, 831, 847, 851, 852; 430/270, 312, 315; 437/180, 181, 187, 226; 607/5, 129

[56] References Cited

U.S. PATENT DOCUMENTS

| | | | |
|---|---|---|---|
| 4,736,521 | 4/1988 | Dohya | 29/830 |
| 5,058,250 | 10/1991 | Turnbull | 29/25.35 |
| 5,504,036 | 4/1996 | Dekker et al. | 437/183 |

FOREIGN PATENT DOCUMENTS

| | | |
|---|---|---|
| 612538 A2 | 8/1994 | European Pat. Off. |
| 3345990 A | 6/1985 | Germany . |
| 8701461 | 12/1987 | WIPO . |
| 9007089 | 6/1991 | WIPO . |

OTHER PUBLICATIONS

PCT International Search Report –Appl.No.: PCT/AU 96/00043 — Jan. 31, 1996.

*Primary Examiner*—W. Donald Bray
*Attorney, Agent, or Firm*—Gottlieb, Rackman & Reisman

[57] ABSTRACT

An elongated implantable electrode assembly includes a set of electrode pads arranged in a pre-selected pattern, and a plurality of longitudinal wires, each wire being connected to at least one pad. The electrode assembly is formed by first depositing the pads on a sacrificial layer, adding wires to the pad, embedding the pads and wires in a carrier and then removing the sacrificial layer. These steps can be performed using photolithographic techniques.

14 Claims, 7 Drawing Sheets

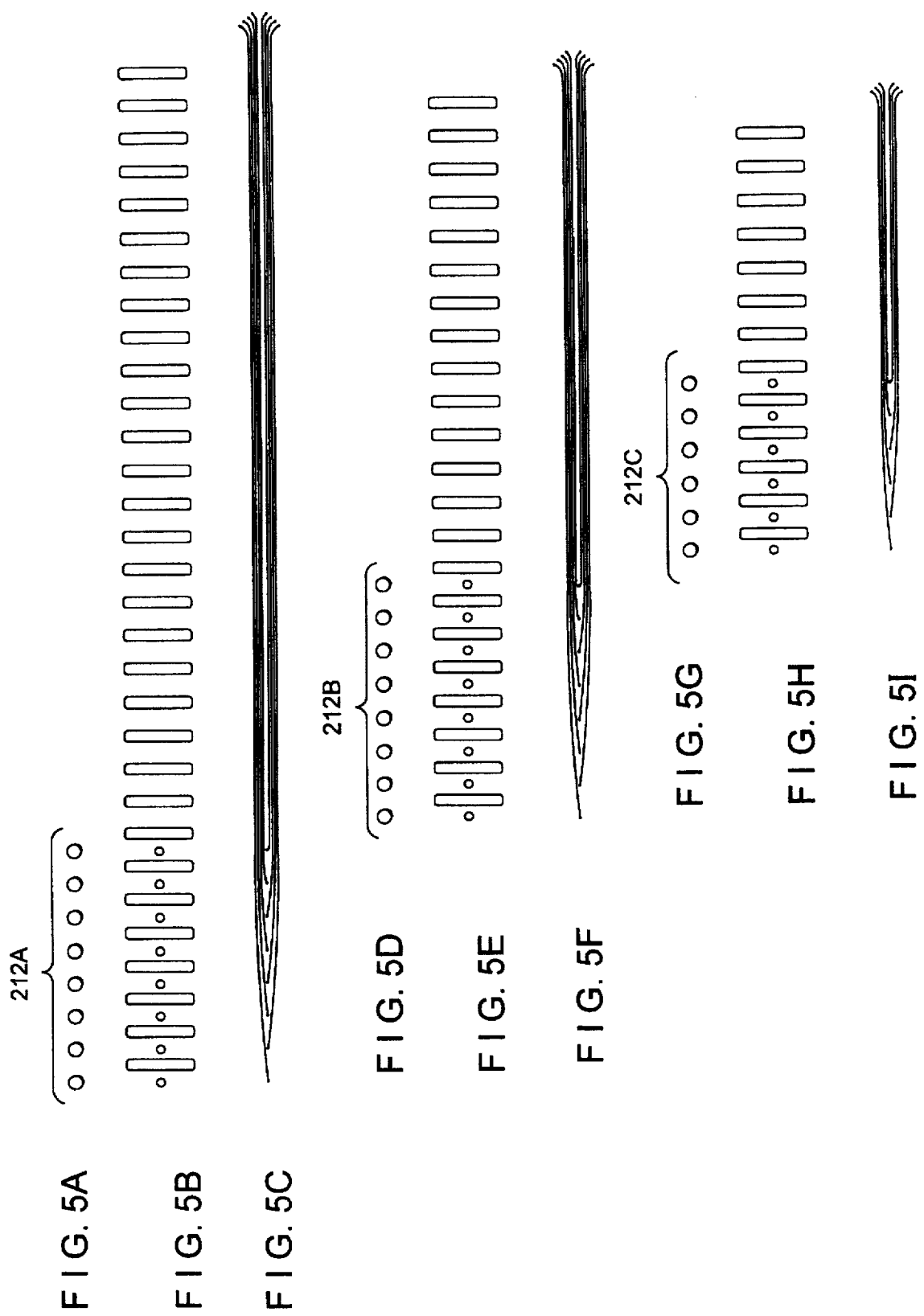

THIN FILM FABRICATION TECHNIQUE FOR IMPLANTABLE ELECTRODES

BACKGROUND OF THE INVENTION

A. Field of Invention

This invention pertains to a method of making electrodes particularly suited for implantation into an organism, using thin film technology normally used for the manufacture of integrated circuits.

B. Description of the Prior Art

A microelectrode system for neural stimulation or recording consists of a series of conducting pads which are placed close to the target neurones. The pads are connected to recording or stimulating electronics via conductors which are insulated from each other and from the surrounding medium. One such electrode arrangement which is in common use today is made by the Cochlear, Pty., Ltd. Of Lane Cove, N.S.W., Australia, under the name Cochlear Implant CI22M. This device consists of a number of platinum rings or balls positioned along a flexible insulating carrier, generally made from silicon rubber. Attempts to use thin film processing techniques to fabricate these electrodes have failed to produce a reliable electrode suitable for use in humans. For example, electrodes have been constructed with silicon substrates. These micromachined devices may be suitable for cochlear implant electrodes. See Frazier AB, Ahn CH, Allen MG, "Development of micro machined devices using polyamide-based processes" Sensors and Actuators 1994; A45; 47–55. However, they are extremely thin (5–15 μm) in order that they can be flexible enough to be inserted into the cochlea. Because of this extremely small dimension, these electrodes are very brittle and difficult to handle.

In general, the reason why thin film techniques have not been applied to commercial cochlear electrode production or the production of other neural electrodes lies in the difficulty of selecting materials which are compatible with both the processing techniques and with the target tissue in which the device has to be used. The choice of conductor is limited to noble metals such as platinum or iridium.

There are much wider choices in the insulating material, but the following properties must be maintained:
1. Biocompatibility
2. Stability to the processes that are used to fabricate the metalization patterns.
3. Flexibility and mechanical compatibility with the target organ.

So far, materials which adequately fulfil the requirements of point 1 and 2 above do not have the required mechanical properties of point 3. Thus clearly there is a need for an improved technique for commercial production of electrodes, such as cochlear implants, and the like, which can be used relatively inexpensively and efficiently, taking advantage of photolithographic techniques.

OBJECTIVES AND SUMMARY OF THE INVENTION

In view of the above, it is an objective of the present invention to provide a method of making implantable electrode systems or arrays using thin film technology.

A further objective is to provide a technique which can be used to make electrode systems repeatedly with guaranteed accuracy and repeatability.

A further objective is to provide a technique which can be performed using automatic machinery thereby dispensing with the need for manual labor.

Other objectives and advantages of the invention shall become apparent from the following description of the invention.

The application of thin film techniques has obvious advantages over the more laborious, time consuming hand assembly techniques. Thin film photolithographic techniques can be used to fabricate small structures rapidly with higher density of electrodes than is possible with hand assembly.

This disclosure addresses the problems mentioned above by describing a process which allows the conductors to be formed by photolithographic processes. Elastomeric insulation is then added to free standing conductor patterns thus formed. This technique has the added advantage that the metal-polymer adhesion can be more easily optimized as the polymerization is a low energy process. Achieving a good adhesion between metal films and polymer supports is essential to maintaining the mechanical integrity of the device. Most metal deposition processes intrinsically require high energy levels. For instance, in thermal evaporation or sputtering metal atoms are used which have a high energy level when they impact the polymer surface. Chemical rearrangements which occur as a result of this bombardment lower the metal polymer adhesion. A solution proposed herein is to add the polymer to the metal rather than the other way around. The following is a description of a process based on standard thin film techniques which allows this to be done. The technique is illustrated with a cochlear implant electrode but other neural stimulating or recording electrodes could be made in a similar way.

Briefly, in accordance with this invention, an electrode array suitable for implantation into a patient's body consists of a plurality of electrode pads disposed in a preselected pattern and imbedded into an elongated carrier made of a relatively stiff, non-conductive material. The carrier must be sufficiently rigid to allow the electrode assembly to be inserted smoothly into the body of a patient through an incision made for this purpose, or through a natural cavity or opening. Preferably the carrier has a minimal cross-section to ensure that during implantation, it requires only a small incision or opening, and that it does not interfere with the patient's tissues. The carrier includes a distal end adjacent to which at least some of the pads are disposed, and a proximal end. A plurality of connecting wires extend through the carrier body from the pads to the proximal end. At the proximal end, these wires are connected by coupling means to electronic circuitry for sending to and/or receiving electrical signals from the pads.

Importantly, a photolithographic process is used to produce the electrode assembly using a sacrificial layer as the initial base. More particularly, first, pads are formed on the base in the preselected pattern. Next, pad connectors are added to the pads. The third step consists of forming wires extending from the pad connectors to the proximal end. The wires, connectors and pads are then embedded or encapsulated in a plastic sheath which forms the carrier, and the base is eliminated.

Optionally, the wires are formed with reinforcing zones constructed and arranged to allow the wires to flex during manufacture and implantation without breaking by providing strain relief. These zones advantageously also provide a strong bond with the encapsulating sheath.

BRIEF DESCRIPTION OF THE DRAWINGS

FIGS. 5A–I show the masks used to make an electrode assembly in accordance with a second embodiment;

DETAILED DESCRIPTION OF THE INVENTION

Generally, electrode production is carried out on a sacrificial layer made of a material selected to withstand all of the conditions of the processing steps but which can be removed by dissolution, by peeling or by heating.

The electrode pads, electrode and wires are formed by a photolithographic technique, mainly by plating platinum or another suitable metal through a polyimide mask. The process relies on a combination of three basic techniques:

1. Thermal or electron-beam evaporation of platinum;
2. Masking and etching; and
3. Film thickening by electrolytic deposition.

Alteratively, platinum can be deposited directly on a copper substrate through the desired mask by electroplating.

Each wire is attached to an electrode pad through connectors. The connectors are arranged so that when the polyimide mask is removed the wires will be self-supporting in mid-air. Preferably the wires are formed with steps or flexible zones etched into the polyamide to improve electrode longitudinal flexibility and facilitate structure encapsulation in the corner.

The polyimide in the structures can be removed by either plasma etching or by chemical etch.

A polymer backing, parylene or silicone rubber, is then added to the free standing electrode structure in two steps. Firstly, the back of the electrode is formed, then the sacrificial layer (e.g., copper substrate) is removed. If the sacrificial layer is a material which can be etched then it is possible that the polymer may be added in just a single step. This is achieved by forming a channel in the substrate material with a simple undercut etch.

Figure 1A:
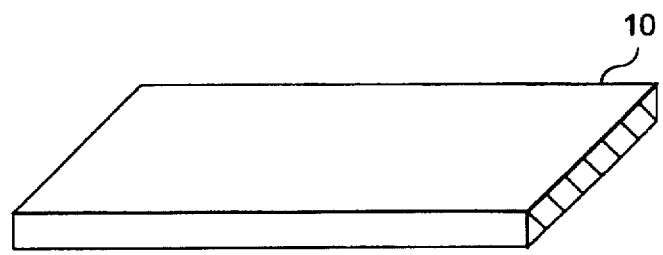
FIGS. 1A–1I show in perspective the steps of making an electrode assembly in accordance with this invention.
Figure 2A:
FIGS. 2A–F shows a side sectional view of the electrode assembly during some of the steps of FIG. 1.
Figure 3:
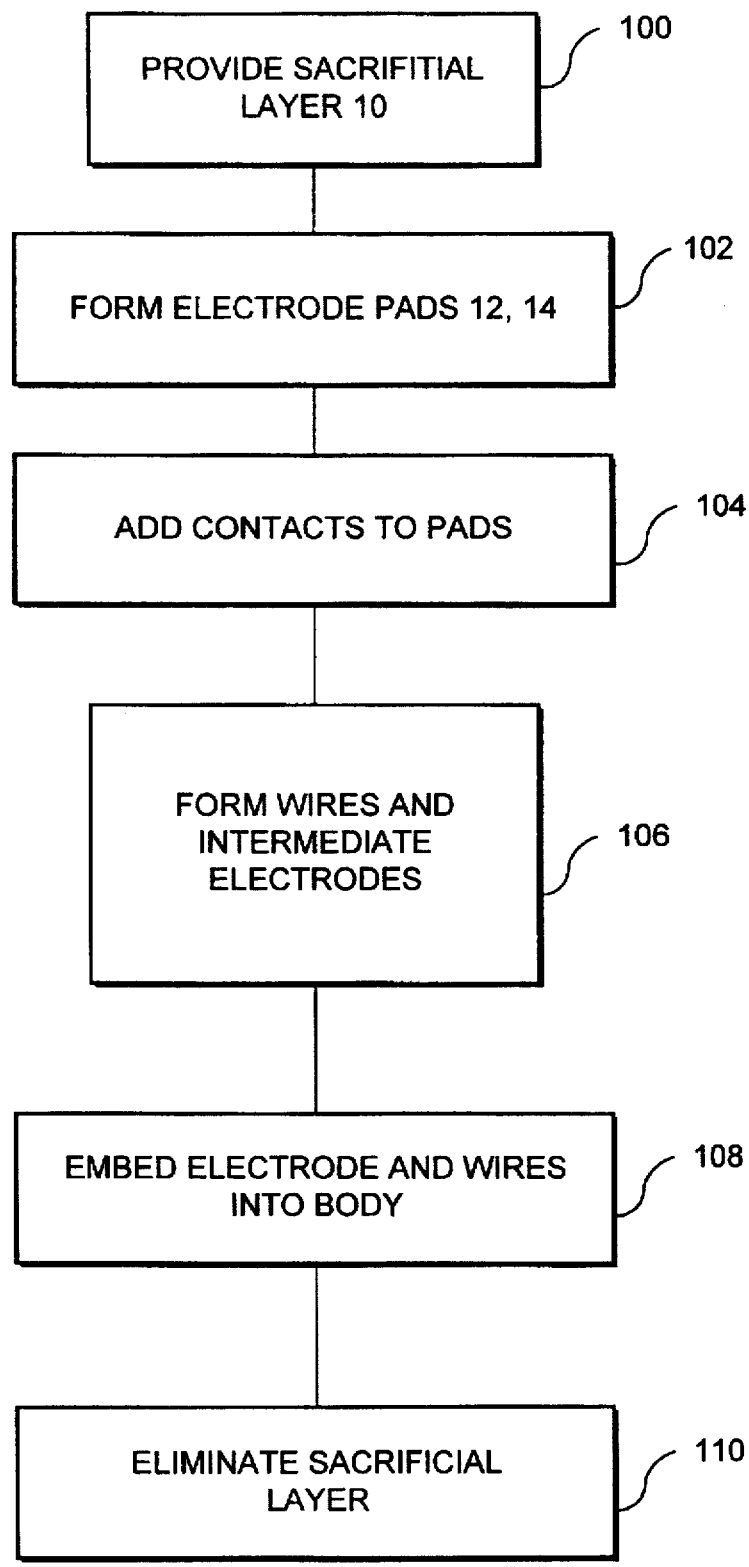
FIG. 3 shows a flow chart for the subject method.

Referring now to the Figures, in order to make an electrode assembly, in accordance with this invention, first, a sacrificial layer 10 is provided, made for example of polished copper (step 100) (FIGS. 1A, 2A, and 3). This layer must have a thickness selected so that it is strong enough to withstand the chemical action the other processing steps require to manufacture the electrode assembly.

Figure 1B:
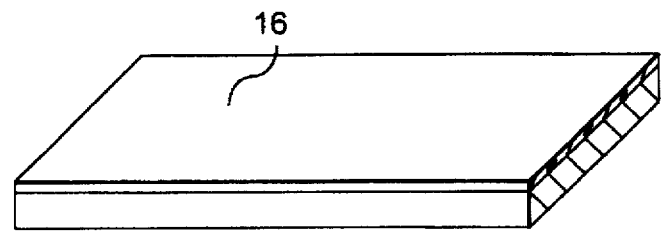
Figure 1C:
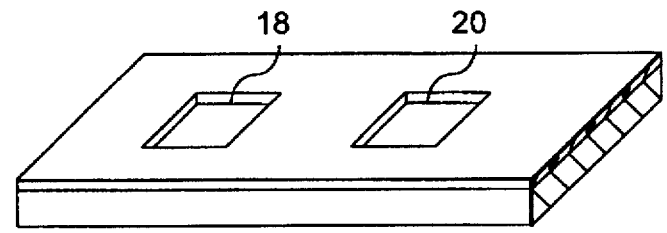
Figure 1D:
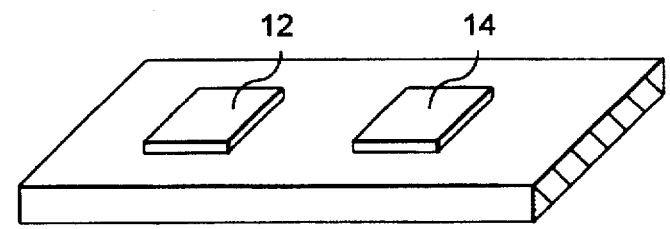

Next, a plurality of electrode pads 12, 14 are formed on layer 10 (step 102). These pads are preferably made of a highly conductive biocompatible, material such as platinum, iridium or other similar material. As previously mentioned, preferably the pads are formed on layer 10 using thin film techniques well known in the art of manufacturing integrated circuits. More specifically, as shown in FIGS. 1B–1D, step 102 consists of a number of substeps. First, (FIG. 1B) the layer 10 is covered, for example by spinning, with a thin layer 16 of photopolymerisable polymeric (PR) material. Next, a photolithographic technique is used to make apertures 18, 20 in layer 16, having the dimensions of the pads 12, 14. The photolithographic technique involves applying a mask (not shown) to the layer 16, exposing the mask and layer 16 to light having a specific wavelength, removing the mask, and developing the layer 16 to dissolve the portions exposed to light to generate the apertures 18, 20. These steps are well known in the art and need not be described in more detail herein.

Figure 2B:
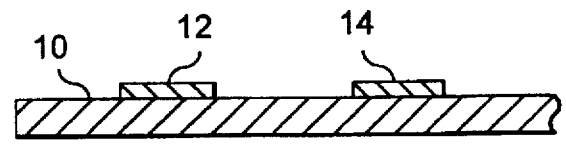

Next, platinum is applied to layer 16, for example by sputtering, or thermal electron-beam evaporation to form the pads 12, 14 in holes 18, 20. Finally, the layer 16 is dissolved leaving the pads 12, 14, as shown in FIGS. 1D and 2B.

Alternatively, pads 12, 14 could be formed by applying a mask onto layer 10, electroplating platinum through apertures in the mask, and then removing the mask.

Figure 1E:
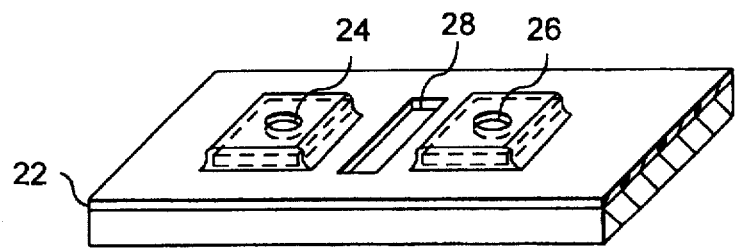
Figure 1F:
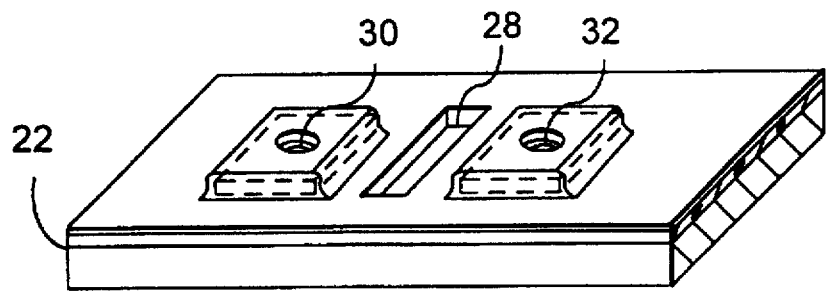
Figure 1G:
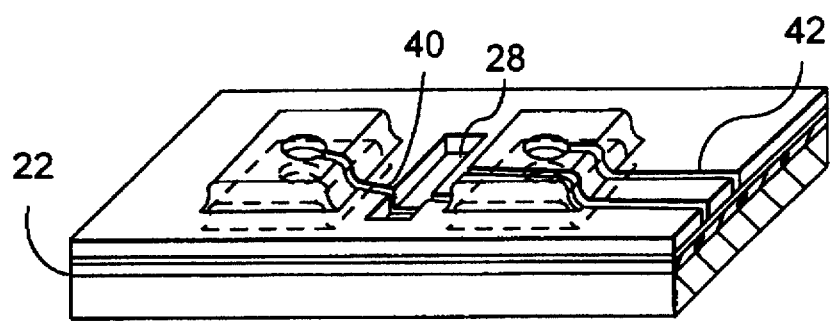
Figure 2C:
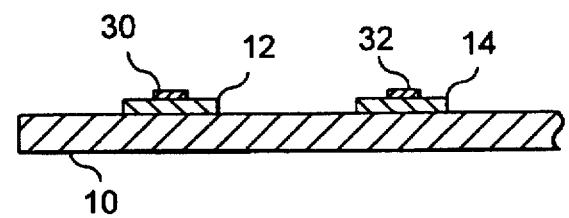

In the following step 104 the pad contacts are added. This step 104 is performed essentially by repeating the substeps used to form pads 12, 14. As shown in FIG. 1E, first a layer 22 of PR is applied to both layer 10 and pads 12, 14. Next, two round apertures 24, 26 are formed in layer 22 on top of pads 12, 14. A third aperture 28 is also formed on top layer 10 in a location between pads 12, 14, as shown in FIG. 1E. Next, platinum is deposited (FIG. 1F), for example by vacuum or by electroplating in apertures 24, 26 for making contacts 30, 32. The resulting structure is shown in FIG. 2C.

Figure 1H:
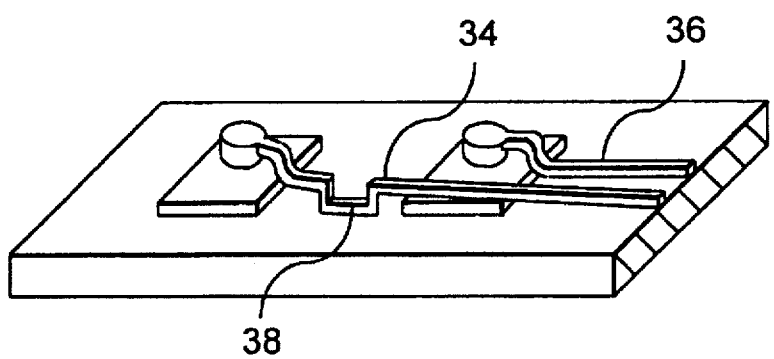
Figure 2D:
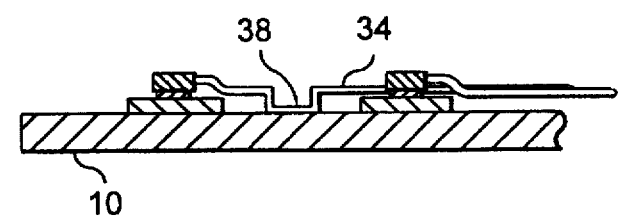

Next, as indicated by step 106, the wires 34, 36 for the pads 12, 14, as well as a reinforcing zone 38 are formed. For this purpose, channels 40 and 42 are etched by using another lithographic mask (not shown). Channel 40 leads from contact 30 to a proximal end of the assembly (not shown) and channel 42 leads from contact 32 also to the proximal end. Next, platinum is introduced into the channels 40 and 42, for example, by electroplating. Finally, layer 22 is removed, leaving the structures shown in FIGS. 1H and 2D. Importantly, the wire 34 includes a step which dips down toward layer 10 and goes back up again, as best seen in FIG. 2D, thereby forming a reinforcing or flexible zone 38. This step strengthens the wire 34 so that it is substantially self-supporting as it extends through the air above pad 14.

In the steps described above the PR may be removed by either plasma etching or by chemical etch.

Figure 2E:
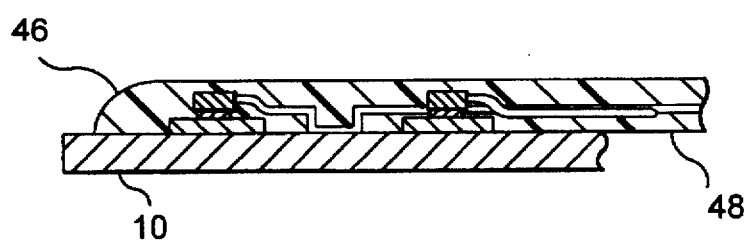

Next, an insulating material 46, made for example of parylene or silicone rubber is applied on the pads 12, 14, contacts 30, 32 and wires 34, 36 to embed the same and form a cohesive elongated body 48 (step 108, FIG. 2E).

Figure 1I:
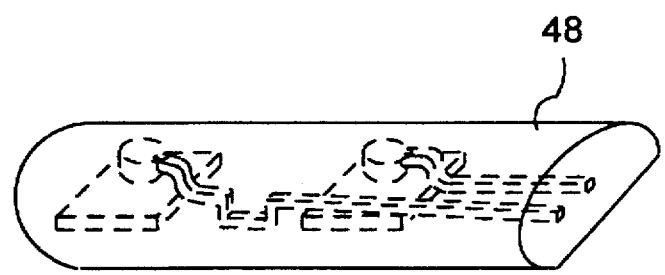
Figure 2F:
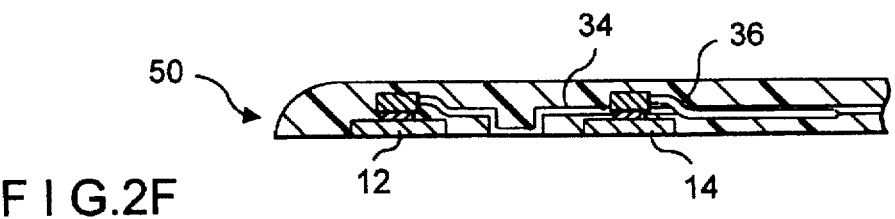

Finally (step 110), the sacrificial layer 10 is removed, leaving the completed electrode assembly 50 (FIGS. 1I, 2F). The material 46 may be further molded to or laminated to a preselected shape.

FIGS. 1 and 2 show the steps for making the electrode assembly at a microscopic level. FIGS. 4A–C and FIGS. 5A–J show two different schemes for making the electrode assembly at a microscopic level.

Figure 4A:
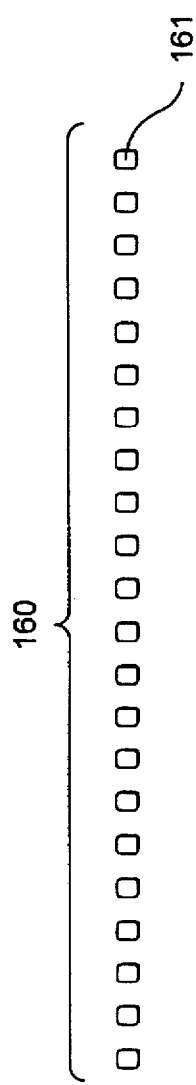
FIGS. 4A–C show the masks used to make an electrode assembly in accordance with a first embodiment of the invention.
Figure 4B:
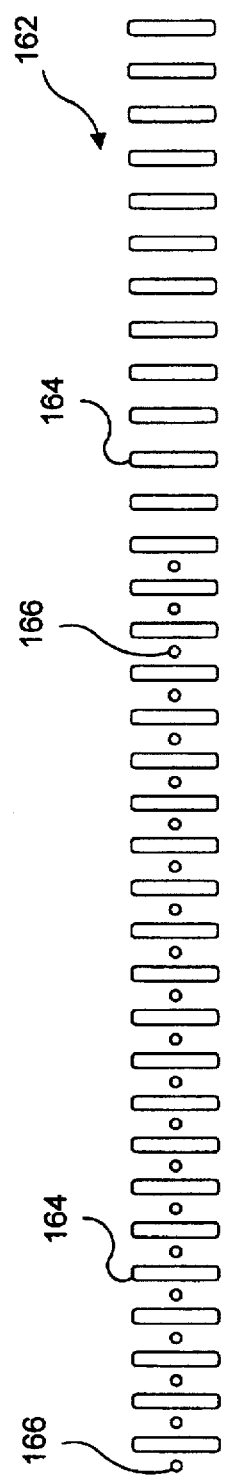
Figure 4C:
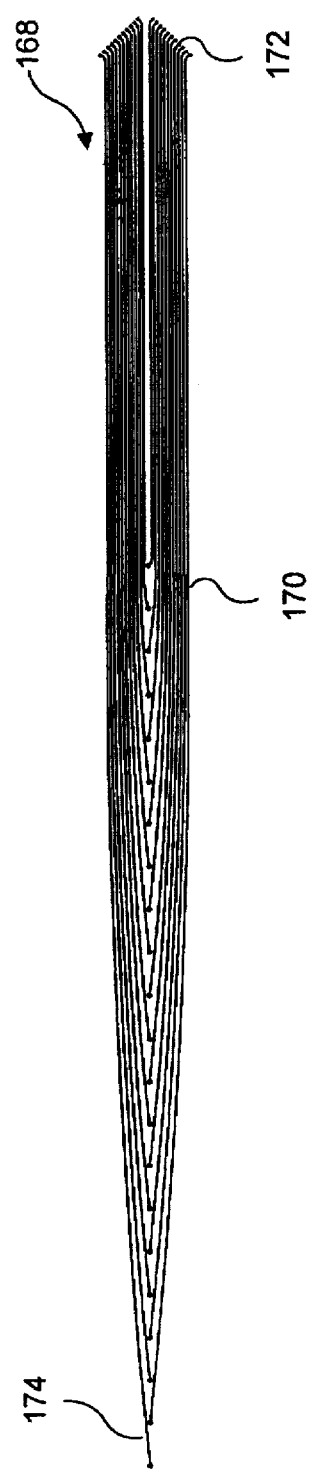

More particularly, FIGS. 4A–C show some of the masks used to make the apertures of FIGS. 1 and 2 and their respective relationship. FIG. 4A shows mask 160 with square zones 161. This mask is applied to layer 16 (FIG. 1B) to generate the holes 18, 20.

FIG. 4B shows a mask 162 consisting of a plurality of bar shaped zones 164. At the distal end, the mask 162 is formed with round 166. This mask is used to generate the apertures 24, 26 and 28 in FIG. 1E which result respectively in contacts 30, 32 and steps 38. Each zone 164 forms a step 38.

FIG. 4C shows a mask 168 used to generate the longitudinal apertures 40, 42, (FIG. 1G) which generate the wires 34, 36 (FIG. 1H) As seen in FIG. 4C, the mask includes several substantially parallel dark lines 170. Each line 170 includes a proximal end 172 for connection to an outside terminal (not shown) and a distal end 174 electrically coupled to a connector such as 30. Thus, each pad is connected to a corresponding wire extending through the length of the electrode system 50.

The process described above may be used to manufacture an electrode assembly having a large number of electrodes. For example, in FIGS. 4A–4C the masks can be used to make an assembly with 22 electrodes, wherein the wires are all arranged essentially in a common layer.

Figure 5J:
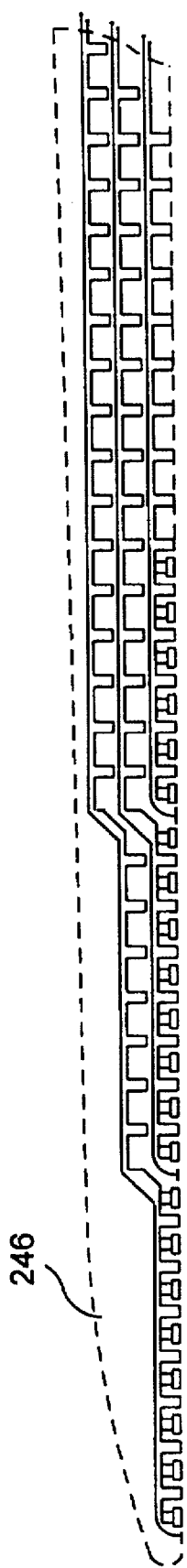
FIG. 5J shows a cross sectional view of an electrode assembly constructed by using the masks of FIGS. 5A–I.

However, for an assembly with a larger number of electrodes and/or if the electrode assembly must be limited in cross-sectional area, a multilayered approach is necessary. FIGS. 5A–5J show the masks for making a 22-electrode assembly in three layers. FIGS. 5A–5C and 5D–5F show the layers for eight electrodes each, while FIGS. 5G–5I show the masks for six additional electrodes. Preferably the bases of masks in FIGS. 5B, 5E and 5H are aligned so that the steps formed in the wires are superimposed as shown in the cross-sectional view of FIG. 5J of an electrode assembly made using the masks of FIGS. 5A–I.

In this embodiment, the electrodes are made in three different sets, marked in the figures as 212A, 212B and 212C, each being provided with their own connector pads and wires by using the techniques described for the embodiment of FIGS. 4A–4C. After the three sets are completed, they are disposed in a juxtaposed position, and sandwiched as shown in FIG. 5J. Thereafter, sheath 246 is applied to form the electrode carrier.

Figure 6:
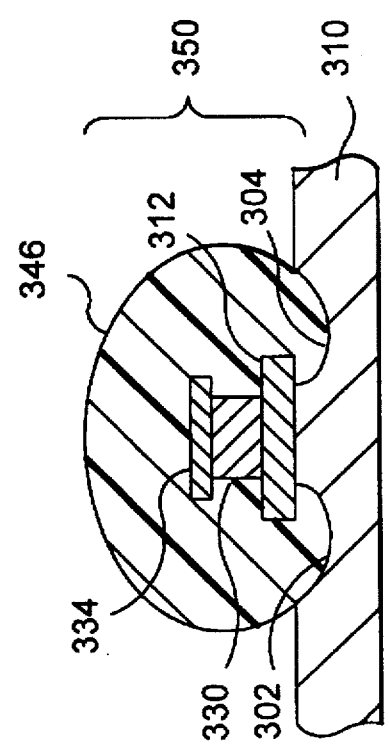
FIG. 6 shows a cross-sectional view of an alternate embodiment of the invention.

In an alternate embodiment of the invention shown in FIG. 6, sacrificial layer 310 is made of a material which can be etched so that two grooves 302, 304 are formed therein prior to the formation of the electrode assembly. The electrode assembly includes electrode 312, connector 330 and wire 334, all disposed in a sheath or carriers 346. The carrier 346 is formed around the electrodes, connectors and wires, such that it flows into the grooves 302, 304. Similar grooves are formed and filled with insulating material underneath reinforcing zones 38 (FIGS. 1H and 2D) of the wires. After the carrier is set, the whole electrode assembly 350 can be peeled off sheet 310 in a single step.

The current electrode production techniques rely on tedious and costly hand assembly techniques. The photolithographic techniques disclosed herein provide several distinct advantages:

1. Low cost and increased throughput of devices;
2. Much higher density electrodes possible;
3. Costly hard tooling (e.g., molds) can be eliminated; and
4. Flexible and rapid design cycles.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A method of making an elongated implantable electrode assembly comprising the steps of:
   providing a sacrificial layer;
   forming a plurality of pads on said sacrificial layer, said pads being made of an electrically conducting, biocompatible material;
   forming a plurality of wires, each wire being connected to at least one of said pads;
   embedding said pads and said wires in an electrically nonconductive material to form an assembly body; and
   removing said sacrificial layer from said body;
   wherein said pads and wires are formed by lithographic techniques.

2. The method of claim 1 wherein said pads and wires are formed of platinum.

3. The method of claim 1 further comprising the step of forming pad connectors between said wires and corresponding pads.

4. The method of claim 1 further comprising forming in said wires reinforcing zones.

5. The method of claim 4 wherein said zones are longitudinally offset.

6. A method of forming an electrode assembly having a plurality of electrodes and wires extending longitudinally through the assembly and connected through said electrodes, said method comprising the steps of:
   forming said wires using lithographic techniques;
   forming a carrier about said wires, said carrier being made of a flexible non-conducting material; and
   removing said sacrificial layer.

7. The method of claim 6 further comprising forming pads on said sacrificial layer using lithographic techniques in a pre-selected pattern, each wire being connected to a corresponding pad.

8. The method of claim 7 wherein said pads are formed substantially simultaneously.

9. The method of claim 7 wherein said pads are partitioned into a number of sets, said method comprising forming the sets of pads separately, each set having its own wires, and then assembling said sets.

10. The method of claim 6 wherein said wires are formed with reinforcing zones.

11. The method of claim 10 wherein said reinforcing zones are formed by forming steps in said wires at predetermined locations.

12. A method of making an elongated implantable electrode assembly comprising the steps of:
   providing a sacrificial layer;
   forming a plurality of pads on said sacrificial layer, said pads being made of an electrically conducting, biocompatible material;
   forming a plurality of wires, each wire being connected to at least one of said pads;
   embedding said pads and said wires in an electrically nonconductive material to form an assembly body; and
   removing said sacrificial layer from said body;
   wherein said wires and pads are formed of a material selected from the group of platinum and iridium.

13. A method of making an elongated implantable electrode assembly comprising the steps of:
   providing a sacrificial layer;
   forming a plurality of pads on said sacrificial layer, said pads being made of an electrically conducting, biocompatible material;
   forming a plurality of wires;
   forming pad contacts, each wire being connected to at least one of said pads by a pad contact;
   embedding said pads and said wires in an electrically nonconductive material to form an assembly body; and
   removing said sacrificial layer from said body.

14. A method of making an elongated implantable electrode assembly comprising the steps of:

providing a sacrificial layer;

forming a plurality of pads on said sacrificial layer, said pads being made of an electrically conducting, biocompatible material;

forming a plurality of wires, each wire being connected to at least one of said pads;

embedding said pads and said wires in an electrically nonconductive material to form an assembly body; and removing said sacrificial layer from said body;

wherein at least some of said wires are formed with reinforcing zones.

* * * * *